US011522991B2

(12) United States Patent
Minzer

(10) Patent No.: US 11,522,991 B2
(45) Date of Patent: *Dec. 6, 2022

(54) MEDICAL ALERT DEVICE

(71) Applicant: Futurama Marketing, LLC, Brooklyn, NY (US)

(72) Inventor: Sam E. Minzer, Brooklyn, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/154,080

(22) Filed: Jan. 21, 2021

(65) Prior Publication Data

US 2021/0228162 A1    Jul. 29, 2021

Related U.S. Application Data

(60) Provisional application No. 62/966,075, filed on Jan. 27, 2020.

(51) Int. Cl.
*H04M 1/72424* (2021.01)
*H04W 4/24* (2018.01)
*H04M 1/72466* (2021.01)
*H04W 4/90* (2018.01)
(Continued)

(52) U.S. Cl.
CPC ....... *H04M 1/72424* (2021.01); *A61B 5/0004* (2013.01); *A61B 5/0022* (2013.01); *A61B 5/1112* (2013.01); *A61B 5/1117* (2013.01); *A61B 5/6831* (2013.01); *A61B 5/7405* (2013.01); *A61B 5/746* (2013.01); *A61B 5/747* (2013.01); *H04M 1/72466* (2021.01); *H04W 4/24* (2013.01); *H04W 4/90* (2018.02)

(58) Field of Classification Search
CPC combination set(s) only.
See application file for complete search history.

(56) References Cited

U.S. PATENT DOCUMENTS 5,638,438 A * 6/1997 Keen ................. H04M 1/27475
                                                         379/354
D667,003 S  * 9/2012 Richter ..................... D14/253
9,214,078 B1* 12/2015 Seese ................. G08B 21/0484
(Continued)

OTHER PUBLICATIONS

Panosonic Operating Instructions, 2008, Panasonic Communications Company, LTD. (Year: 2008).*
(Continued)

*Primary Examiner* — Nabil H Syed
*Assistant Examiner* — Cal J Eustaquio
(74) *Attorney, Agent, or Firm* — Frost Brown Todd LLC

(57) ABSTRACT

A medical alert device that may be used to transmit a medical alert over a wireless network. The medical alert device includes a microprocessor for controlling the operation of the device, a data store configured to store the phone number of at least one predetermined call recipient, and a wireless communication module that is connectable to a wireless network. The medical alert device also includes a preprogrammed user actuatable button that is configured to, upon being actuated, initiate the execution of software instructions by the microprocessor to retrieve a phone number stored on the data store. The microprocessor may then connect to the wireless network and establish a communication link with the predetermined call recipient by dialing the phone number. Also disclosed are peripheral devices that may be operatively connected to the medical alert device.

17 Claims, 9 Drawing Sheets

(51) Int. Cl.
*A61B 5/00* (2006.01)
*A61B 5/11* (2006.01)

(56) References Cited

U.S. PATENT DOCUMENTS

| | | | | |
|---|---|---|---|---|
| 2006/0252457 A1* | 11/2006 | Schrager | ............ | H04M 1/6066 |
| | | | | 455/556.1 |
| 2008/0102785 A1* | 5/2008 | Childress | ............. | H04W 4/029 |
| | | | | 455/404.1 |
| 2013/0307685 A1* | 11/2013 | Sholder | ............... | A61B 5/6843 |
| | | | | 340/539.12 |
| 2018/0249015 A1* | 8/2018 | Nakano | ............... | H04M 15/852 |
| 2019/0119954 A1* | 4/2019 | Wyatt | .................... | E05B 67/38 |

OTHER PUBLICATIONS

Branch, Philip, "Curious Kids: How do SIM cards make a hone work?", The Conversation, p. 2. (Year: 2018).*

* cited by examiner

MEDICAL ALERT DEVICE

CROSS-REFERENCE TO RELATED APPLICATION

This application is a nonprovisional patent application that makes a priority claim to U.S. Provisional Application No. 62/966,075 filed Jan. 27, 2020, the disclosure of which is hereby incorporated by reference as if fully restated herein.

TECHNICAL FIELD

Exemplary embodiments of the present invention relate generally to medical alert devices that utilize limited use SIM cards and are configured to transmit a medical alert directly to an emergency dispatch office.

BACKGROUND

Personal emergency response systems (PERS) are commonly employed to provide a measure of safety and security to their users. PERS typically include a communication device and a subscription to a monitoring plan. By paying for the subscription, usually on a monthly or annual basis, the subscriber may utilize the communication device to transmit a medical alert to a remote monitoring station in the event the subscriber is in need of medical attention. The monitoring station, which is commonly owned and operated by the company administering the subscription plan, will then assess the nature of the user's medical alert and, if the personnel at the monitoring station decides to do so, may forward the medical alert to an appropriate responder. In many cases, the monitoring station will forward the medical alert to a local government operated emergency dispatch center, which is the same responder the subscriber would have reached if the subscriber had simply called 9-1-1. In this sense, the monitoring station exists as an intermediary between the subscriber and the responder. Those skilled in the art will appreciate that in dire situations, having to go through an intermediary could cost precious time that may be critical to the subscriber. What's more, the cost of the subscription for the PERS can often be prohibitively high for many of those who need it most. Considered amongst these people may include, for example, the elderly and the infirm. Many of which may be on low- or fixed-incomes, if at all. Further, it is contemplated that the shortcomings of existing PERS will become more apparent given the continuously rising population of elderly persons worldwide. In the United States alone there are approx. 50 million seniors (aged 65 and older) and this number is projected to grow to approx. 90 million by 2050.

Accordingly, those skilled in the art continue with research and development efforts in the field of personal emergency response systems.

SUMMARY OF THE INVENTION

Disclosed are medical alert devices and systems that may be used to transmit a medical alert.

In one exemplary embodiment of the present disclosure, the medical alert device includes a body that defines an interior space for electronic components, a microprocessor housed within the body that is configured to control the operation of the device, a data store housed within the body that is configured to store the phone number of at least one predetermined call recipient, and a wireless communication module housed within the body that is connectable to a wireless network. Further, the medical alert device also includes a preprogrammed user actuatable button supported by the body that is configured to, upon being actuated, initiate the execution of software instructions by the microprocessor to retrieve a phone number stored on the data store. The microprocessor may then connect to the wireless network and establish a communication link with the predetermined call recipient by dialing the phone number.

In another exemplary embodiment of the present disclosure, the medical alert device includes a body that defines an interior space for electronic components, a microprocessor housed within the body that is configured to control the operation of the device, and a data store housed within the body that is configured to store a phone number of a predetermined call recipient. Further, the medical alert device also includes a reader that is at least partially housed within the body and is configured to receive a subscriber identity module identification card (SIM card), a SIM card that is insertable into the reader and configured to identify and authenticate a user of the device, and a wireless communication module housed within the body that is operable with the SIM card and connectable to a cellular network. Further, the medical alert device also includes a preprogrammed user actuatable button that is supported by the body and is configured to, upon being actuated, initiate the execution of software instructions by the microprocessor to retrieve a phone number stored on the data store. The microprocessor may then connect to the wireless network and establish a communication link with the predetermined call recipient by dialing the phone number.

In yet another exemplary embodiment, medical alert system includes a medical alert device and a charging cradle. The medical alert device includes a body that defines an interior space for electronic components, a microprocessor housed within the body that is configured to control the operation of the device, a data store housed within the body that is configured to store a phone number of a predetermined call recipient, and a wireless communication module housed within the body that is connectable to a wireless network. The medical alert device further includes a preprogrammed user actuatable button supported by the body that is configured to, upon being actuated, initiate the execution of software instructions by the microprocessor to retrieve a phone number stored on the data store, connect to the wireless network, and establish a communication link with the predetermined call recipient by dialing the phone number. The medical alert device further includes a port at least partially housed within the body that is configured to connect the device to a peripheral device. The charging cradle defines a receiving cavity for receiving at least a portion of the medical alert device and includes a coupling feature disposed within the receiving cavity that is configured to couple with the port of the medical alert device when the medical alert device is received in the receiving cavity.

Other examples of the disclosed medical alert devices and systems will become apparent from the following detailed description, the accompanying drawings and the appended claims.

DETAILED DESCRIPTION OF EXEMPLARY EMBODIMENT(S)

Figure 1:
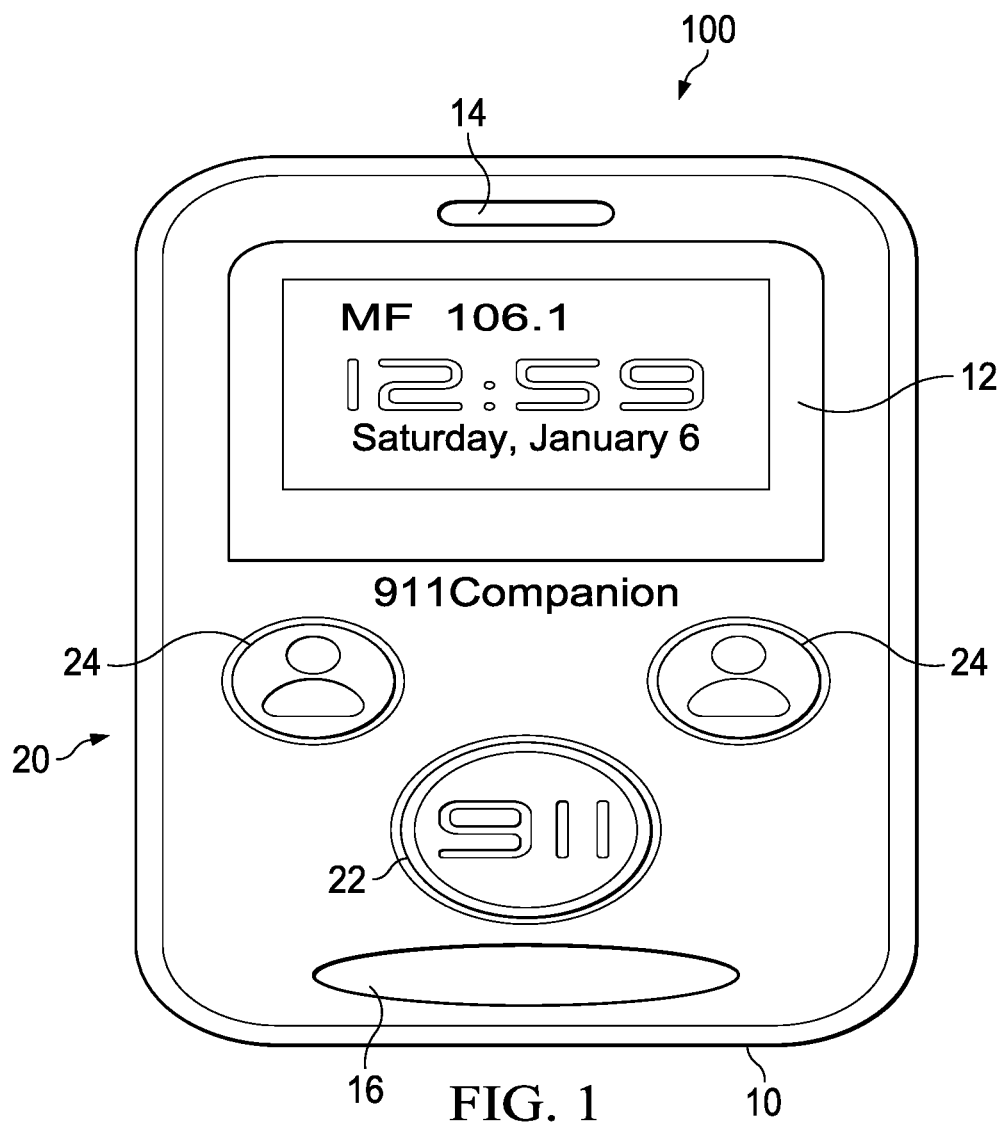
FIG. 1 is a front elevational view of the disclosed medical alert device.

The following detailed description refers to the accompanying drawings, which illustrate specific examples described by the disclosure. Other examples having different structures and operations do not depart from the scope of the present disclosure. Like reference numerals may refer to the same feature, element, or component in the different drawings.

Illustrative, non-exhaustive examples, which may be, but are not necessarily, claimed, of the subject matter according the present disclosure are provided below. Reference herein to "example" means that one or more feature, structure, element, component, characteristic and/or operational step described in connection with the example is included in at least one embodiment and/or implementation of the subject matter according to the present disclosure. Thus, the phrase "an example" and similar language throughout the present disclosure may, but do not necessarily, refer to the same example. Further, the subject matter characterizing any one example may, but does not necessarily, include the subject matter characterizing any other example.

Referring to FIG. 1, the present disclosure provides an embodiment of a medical alert device 100 (herein, the "device") that may be utilized to establish a communication link over a wireless network so that a user may alert a call recipient (e.g., a local government operated emergency response operator) of the user's medical condition. Preferably, the device 100 may be designed with a simplified interface so that the user may quickly select a desired call recipient and initiate a call without much navigation on the device 100. Even more preferably, the device 100 may utilize a low-cost method of wireless communication to better suit the needs of low- or fixed-income users. While the device 100 of FIG. 1 is exemplary, it is not meant to be limiting. The various features of which are described in turn below.

Referring specifically to FIG. 1, the device 100 may include a small, generally rectangular body that defines various sides (i.e., front, back, left, right, top, and bottom). The body 10 may be fabricated out of any suitable material, including polymeric and metallic materials, and may include any suitable configuration of seals, fasteners, and the like to securely house the internal components therein (e.g., within an interior space defined by the body). While the device 100 itself may be fabricated in different sizes and shapes (e.g., circular, rounded, and/or irregular shapes), it is contemplated that the rectangular design may be preferred because the various sides can provide for components/features that enable the user to interface with the device 100, and the small size may be preferred because it lends to the overall portability of the device 100. Ideally, the device 100 may be lightweight and easy to use with one hand.

In one or more embodiments, the body 10 may be coupled to a wearable feature to help keep the device on the user's person. For example, the device 100 may be fixedly connected to a lanyard so that the user may wear the device 100 like a pendant. In another example, the device 100 may be fixedly connected to a watch strap so that the user may wear the device 100 on his/her wrist. In yet another example, the device 100 may be releasably connected to a belt clip so that the user may wear the device 100 on his/her waist. Those skilled in the art will appreciate that various other wearable features may be employed without departing from the scope of the present disclosure.

The front side of the device 100 may be provided with an electronic display screen 12, a plurality of call buttons 20 (e.g., preprogrammed user actuatable buttons), a speaker 14, and a microphone 16. Collectively, these features may enable the user to interface with the device 100 when placing and/or receiving a call. Each call button 20 may be configured to initiate a call to a predetermined call recipient when the call button 20 is actuated by a user (e.g., physically depresses the button). While physically depressible buttons are shown, those skilled in the art will appreciate that touchscreen displays may also be employed without departing from the scope of the present disclosure. A touchscreen display may present actuatable call buttons 20 in the same or in a substantially similar arrangement as the arrangement of call buttons 20 shown. The speaker 14 and the microphone 16 enable the device 100 to receive and broadcast communications, while information about the call may be displayed on the electronic display screen 12.

The display screen 12 may include any suitable type of electronic display screen, such as light-emitting diode displays (LED) and/or liquid crystal displays (LCD), and may be sized and shaped as desired. Typical—but useful—information that may be presented on the display screen 12 can include, for example, device settings (e.g., volume, battery level, wireless connection status, control panels), programmed information (e.g., time, date, contact information), call information (e.g., recipient, caller identity, call duration, missed calls), text messages and the like. In the configuration shown, the display screen 12 may be centered along the width of the body 10 and biased towards the top.

Figure 7:
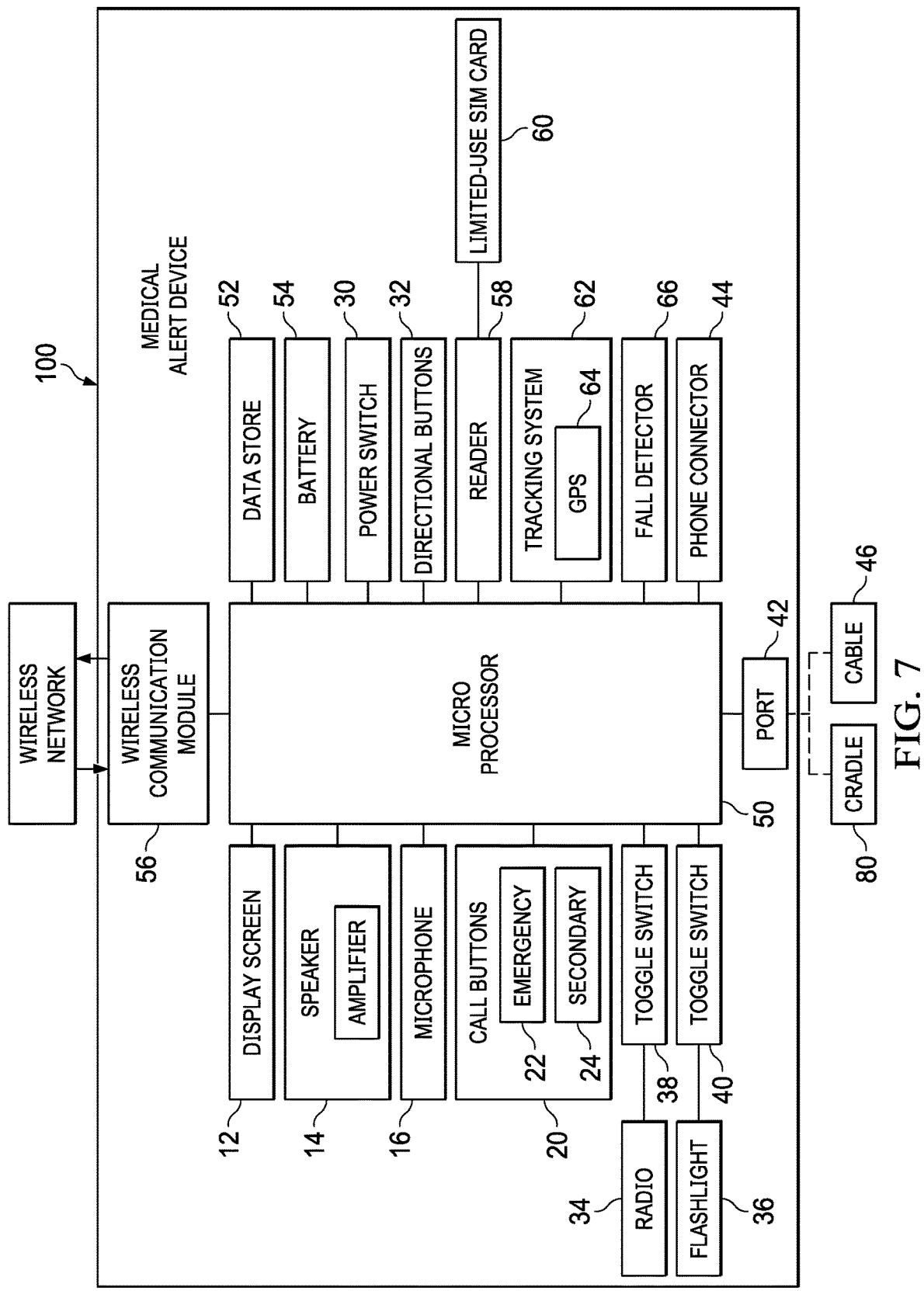
FIG. 7 is a generalized functional block diagram of the internal components of the medical alert device of FIG. 1.

The speaker 14 and the microphone 16 may be centered along the width of the body 10, with the speaker 14 being biased towards the top, above display screen 12, and the microphone 16 being biased towards the bottom, below the emergency call button 22. Like the display screen 12, any suitable speaker and/or microphone may be employed, such as the commercially available speakers and microphones typically used in common cell phones. Preferably, the size and performance of the speaker 14 and the microphone 16 would enable the user to hear and speak while using the device 100 from a distance of at least, for example, about 4 to 18 inches away. If desired, an amplifier 18 may also be provided to increase the volume and sound quality of the audio from the speakers (FIG. 7).

The plurality of call buttons 20 may include an emergency call button 22 and two secondary call buttons 24. While these call buttons 20 are shown as being generally ovular in shape, it is not meant to be limiting as other shapes may be employed, such as puzzle-piece shaped buttons to indicate that the user is autistic. The emergency call button 22 may be centered along the width of the body 10 and biased towards the bottom. The two secondary call buttons 24 may generally be smaller and disposed to the upper left and the upper right of the emergency call button 22. In a preferred embodiment, upon being pressed, the emergency call button 22 may initiate a 9-1-1 call to an emergency dispatch office (e.g., local government operated, private emergency response, etc.), whereas the secondary call button 24 may initiate a call to a predetermined call recipient of the user's choice. Those skilled in the art will appreciate that by pre-programming the emergency call button 22 to directly call an emergency dispatch office (e.g., by dialing 9-1-1), the device 100 may effectively eliminate the need for an intermediary (i.e., monitoring station) between the user and the emergency dispatch office, thereby saving precious time that may be critical to the user. The predetermined call recipient for the secondary call buttons 24 may be, for example, a family member (e.g., a parent), a neighbor, a social worker, a home health aide, a nurse, a doctor, etc. Thus, by providing an emergency call button 22 and secondary call buttons 24, a user of the device 100 may thereby choose an appropriate call recipient based on situational considerations such as, for example, the severity of the user's injuries, the relative closeness (by geographic location) of the potential call recipients, and the like. Those skilled in the art will appreciate that other call button arrangements (including arrangements with either more or less emergency and/or secondary call buttons, arrangements with other types of call buttons, and/or arrangements with the buttons in different locations) may also be utilized.

It is contemplated that the relatively simple design of the device 100, particularly the arrangement of call buttons 20, may enable a quick, easy way of initiating a call. The intuitive nature of this arrangement may be well suited for elderly persons who do not wish to navigate complex user interfaces, or children and the infirm who may have difficulty learning how to do so. Particularly in regards to children, it is further contemplated that parents may prefer the device 100 due to its limited interface (e.g., call buttons 20). The parent may pre-program the call buttons 20 of the device 100 to only initiate calls to recipients approved by the parent.

In one or more embodiments, the device 100 may also be configured to accept incoming calls. Towards this end, the plurality of call buttons 20 may provide for a call button that is configured to accept the call upon being pressed. For example, a secondary call button 24 may be designated for this purpose. Additionally, or alternatively, a dedicated call button may be provided to accept incoming calls. Various other configurations are possible. Furthermore, the device 100 may also be programmed to selectively filter calls such that only calls from pre-designated callers may be accepted (e.g., the call recipients associated with the emergency call button 22 and/or either of the secondary call buttons 24). This functionality may prevent the receipt of unwanted calls (e.g., unsolicited marketing).

In one or more embodiments, the device 100 may include a standard telephone keypad (e.g., a twelve-key arrangement of buttons comprising 0-9 numeric buttons, a star button, and a pound button) or a full QWERTY keyboard provided on the body 10 of the device 100. The call button arrangement shown in FIG. 1 is preferred for its simplicity, but it is understood that a more functional keypad/keyboard may be useful to the user as it would enable the user to manually dial phone numbers and/or send text messages. The inclusion of such will not result in a departure from the scope of the present disclosure.

In one or more embodiments, device 100 may be adapted for use by deaf persons and/or by persons who lack the ability to speak. More specifically, the device 100 may be configured to transmit and receive prerecorded messages (e.g., text and/or voice messages). These messages may be recorded by way of the speaker 14 and microphone 16 or, if provided, a keypad/keyboard on the device 100. Once recorded, these prerecorded messages may be transmitted to a call recipient upon the user pressing one or more of the call buttons 20, or by way of a dedicated button provided on the device.

Figure 2:
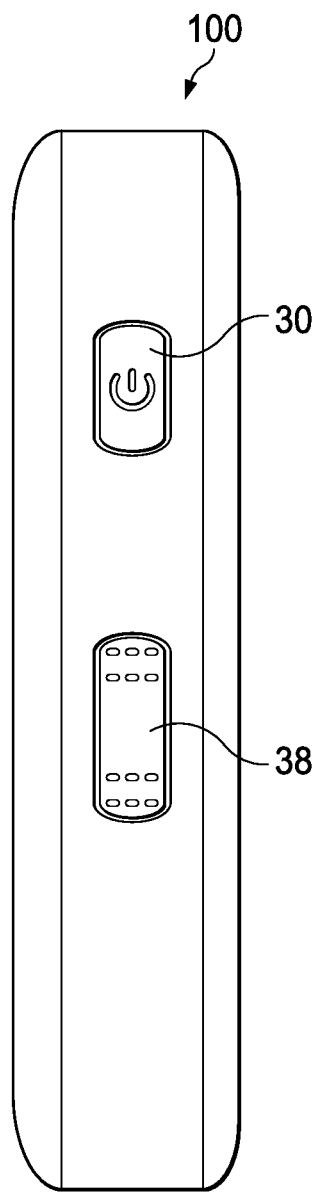
FIG. 2 is a left-side elevational view of the medical alert device of FIG. 1.
Figure 3:
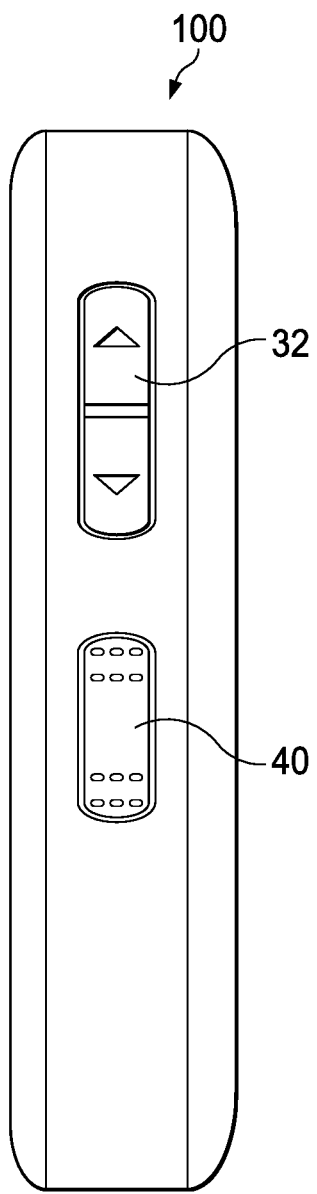
FIG. 3 is a right-side elevational view of the medical alert device of FIG. 1.
Figure 4:
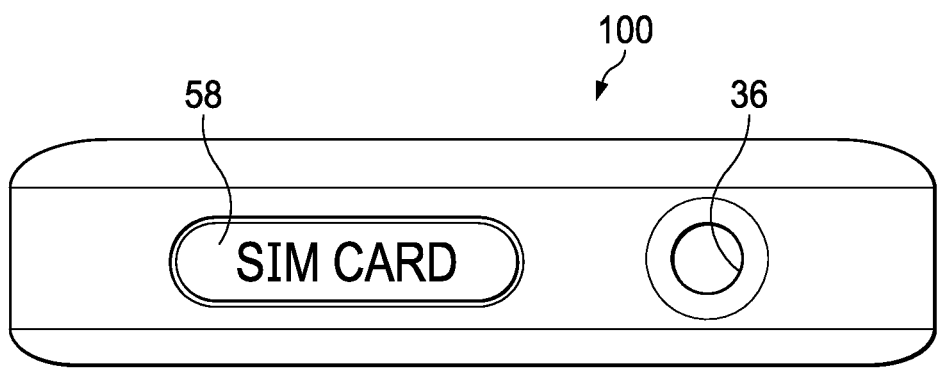
FIG. 4 is a top plan view of the medical alert device of FIG. 1.

Referring to FIGS. 2 and 3, the device 100 may also include a power switch 30 and a pair of up-down directional buttons 32. These buttons 30, 32 may be employed to provide a quick, tactile way of receiving user input. For example, the power switch 30 may be utilized to turn the device 100 on/off, whereas the directional buttons 32 may be used for navigating the user interface (e.g., adjusting volume, scrolling through contact information, etc.). The device 100 may also include a variety of generally useful features such as a radio 34 (FIG. 7) and a flashlight 36 (FIG. 4). A radio 34 included in the device 100 may be configured to receive broadcast signals (e.g., AM and/or FM) in conjunction with the wireless communication module or as a dedicated module. Beyond enjoying music and talk radio, it is contemplated that the radio 34 may enable the user to tune into emergency advisory radio stations as a backup to the call functionality of the device 100 in the event of an electrical blackout or a cellular network failure. In a similar sense, a flashlight 36 may be included to illuminate the user's surroundings in emergency situations, or otherwise as needed. As shown, the right and left sides of the device body 10 may include on/off toggle switches 38, 40 for the radio 34 and the flashlight 36 for quick access. Collectively, these features ensure that the user is not "kept in the dark."

Figure 5:
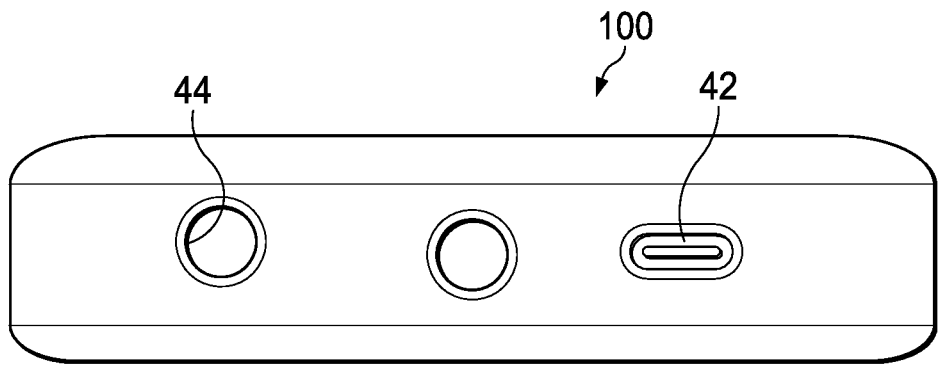
FIG. 5 is a bottom view of the medical alert device of FIG. 1.
Figure 8:
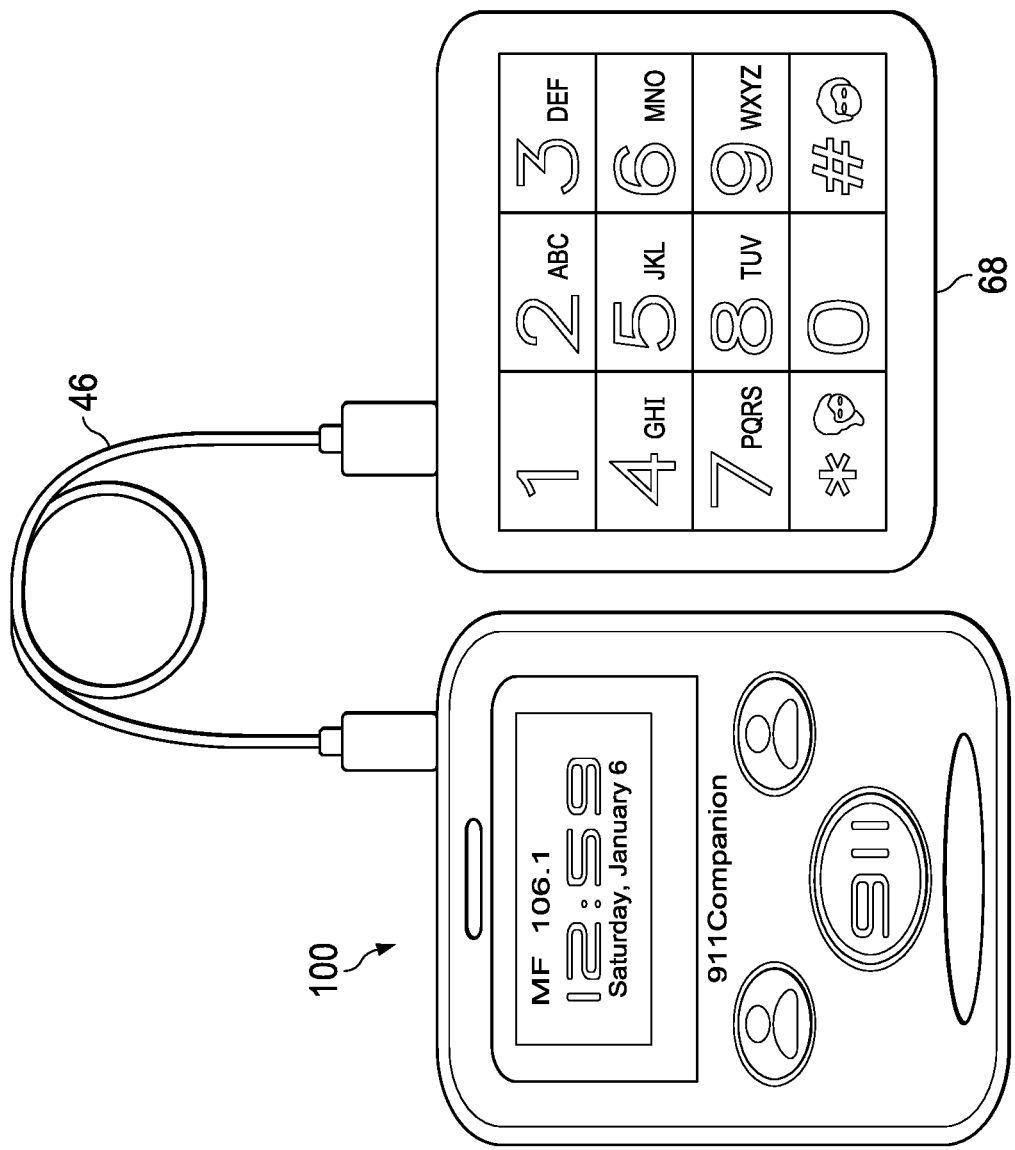
FIG. 8 is a front elevational view of the medical alert device of FIG. 1 connected to a programming pad.

Referring to FIG. 5, the I/O (i.e., input/output) of the device 100 may include a port 42 and phone connector 44 (i.e., headphone jack). Port 42 may utilize any suitable type of connection (e.g., micro USB, USB C, etc.) and may be utilized to charge the device 100 and/or transfer data. An appropriate cable 46 may be provided to establish a connection therefrom (FIG. 8). Phone connector 44 enables the user to plug in headphones and may be provided in a variety of sizes (e.g., standard 2.5 mm, 2.5 mm, and 6.35 mm variants).

Figure 6:
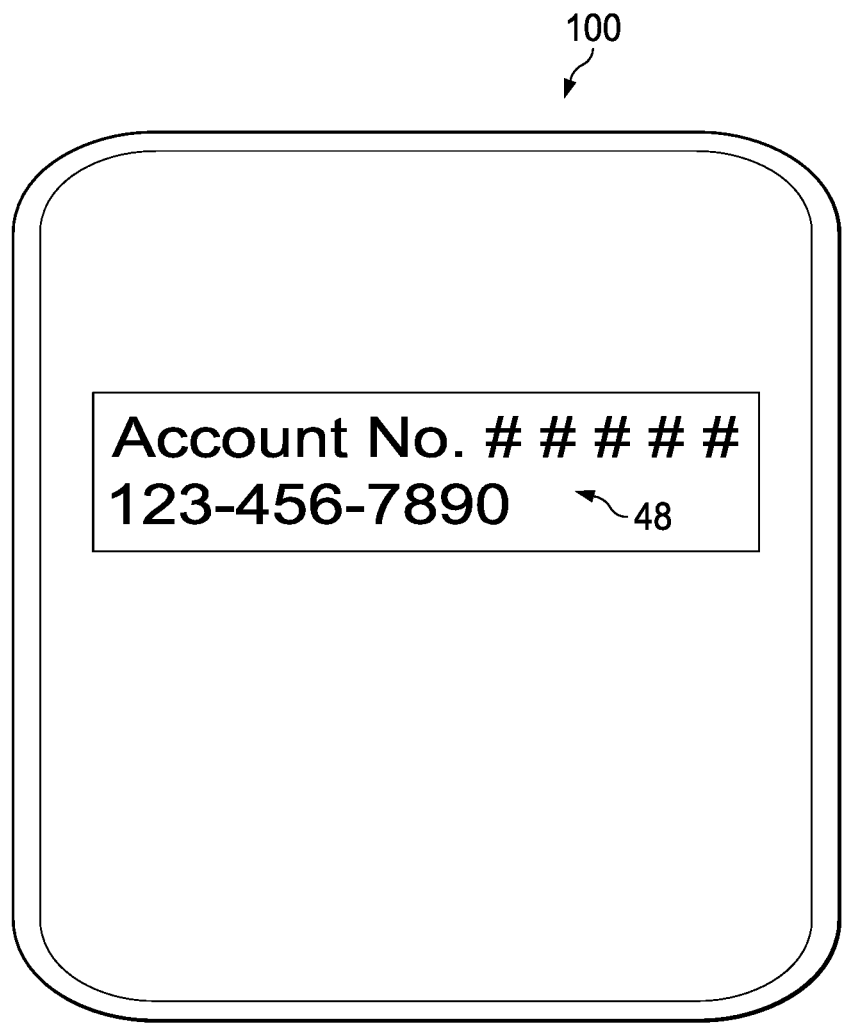
FIG. 6 is a back elevational view of the medical alert device of FIG. 1.

Referring to FIG. 6, the back side of the device 100 may include inscriptions and/or indicia 48 that provide information about the user. These inscriptions and/or indicia 48 may be printed onto sticker paper and affixed to the device 100, or printed directly on the device 100, or etched onto the device 100. In one example, these inscriptions and/or indicia 48 may include an account number associated with the user and a phone number associated with a databank (e.g., such as iCloud, managed by Apple Inc. of Cupertino, Calif., or any other cloud storage management company). The user may provide the databank with the user's personal medical information (e.g., existing medical conditions, medication requirements, etc.), which may then keep this information saved on file. Thus, in the event the user is unconscious or otherwise incapacitated, a first responder, upon locating the device 100 and looking at the back of it, may call the phone number associated with the databank, provide the account information associated with the user, and receive the information on file. Alternatively, in other examples, this personal medical information may be provided directly on the back of the device 100 itself.

Referring now to FIG. 7, the device 100 may function by way of a microprocessor 50, data store 52, battery 54, and wireless communication module 56 (e.g., transceiver). The microprocessor 50 may include any processor or combination of processors capable of performing the functions described by this disclosure. A suitable data store 52 may be selected based on, among other things, the memory requirements of the device components and the amount of data a user is likely to provide. Battery 54 can be any one or more batteries capable of powering the device, including rechargeable and/or traditional single use batteries. In any case, it is contemplated that component and programming solutions will be apparent to those of ordinary skill in the art.

The wireless communication module 56 may connect to a wireless network and attempt to establish a communication link with a call recipient (e.g., by dialing a phone number). Upon doing so, the user may thereby transmit and receive messages (e.g., text messages and/or voice audio) to and from the call recipient. The communication link may be established over any suitable wireless network including cellular phone networks, such as the networks operated by mobile phone service providers (e.g., Verizon, AT&T, Sprint, T-Mobile, etc.), as well as over broadband internet (e.g., voice over internet protocol, by way of WIFI). The wireless communication module 56 may include, for example, an antenna and a receiver, or a transceiver that integrates the two functions. These components are generally commercially available, the suitability of which will be apparent to those of ordinary skill in the art.

Referring back to FIG. 4, the device 100 may include a reader 58 that a user may insert a subscriber identity module identification card (SIM card) into. SIM cards are used to identify and authenticate users of mobile telephony devices. By inserting a SIM card into the reader 58, the device 100 may be enabled to connect to a cellular network. Those skilled in the art will appreciate that various SIM cards may be provided with a range of features (e.g., text messaging, minutes for calling, data, etc.) depending on the plan associated with the SIM card. Some SIM cards provide for the full range of features (e.g., unlimited call/text/data) but generally require a continuing subscription to a cellular plan. Other SIM cards may be more limited in features (e.g., a predetermined number of minutes and texting, no data) but can be purchased with a smaller one-time fee. In one embodiment, the device 100 may be provided with a limited-use SIM card 60 that only allows emergency calls. Such a SIM card 60 may enable the device 100 to place a call to an emergency dispatch office when the user presses the emergency call button 22. In a more preferred embodiment, the limited-use SIM card 60 may also provide for a limited number of calls (expiring thereafter), thereby enabling the secondary call buttons 24 to place calls to predetermined call recipients.

Preferably, the device 100 may also include a tracking system 62 for determining the location of the user. The tracking system 62 may include a dedicated module (e.g., transceiver) or may be provided for in conjunction with the wireless communication module 56. The tracking system 62 may track the user's location by way of a global positioning system 64 (GPS) or a custom geolocation system focusing on local terrain. In practice, the tracking system 62 may transmit the user's location to the call recipient when the user presses a call button 20. Those skilled in the art will appreciate that there may be instances where the user is not able to verbally communicate his/her location (e.g., perhaps the user does not know or due to physical inability). For at least this reason, a non-verbal way of transmitting one's location would find utility.

Optionally, the device 100 may also be provided with a fall detector 66. This fall detector 66 may include any suitable type of sensor such as, but not limited to, accelerometers, impact sensors, combinations thereof, and/or the like. It is contemplated that the device 100 may be configured such that when the user experiences a fall, the fall detector 66 may detect the occurrence of the fall (e.g., commensurate with a threshold level of acceleration or impact), and the device 100 may automatically initiate a call or transmit a message (e.g., a prerecorded voice and/or text message) to the appropriate recipient. If a tracking system 52 is provided, the device 100 may also transmit the user's location to the recipient as well.

The device 100 may be connected to one or more peripheral devices as a way of enabling user input and/or to extend the functionality of the device 100. A peripheral device may be connected to the device by way of a wired connection through port 42, or wirelessly through WIFI and/or Bluetooth. Bluetooth connectivity may be established through the wireless communication module 56 and/or through a dedicated Bluetooth module (e.g., transmitter and receiver, or a transceiver). An exemplary peripheral device that may be connected to the device is a programming pad 68 which may be connected by way of a cable 46 (shown in FIG. 8). While this programming pad 68 is a standard numeric (e.g., 10-key) keypad, different types of programming pads (e.g., full QWERTY keyboards) may also be connected. It is contemplated that this programming pad 68 may enable a user to input user information, such as phone numbers, date/time information, and the like. Other examples of peripheral devices that may be connected include smartphones and computers. These peripheral devices may be connected through the same type of wired connection or, if available, though WIFI and/or Bluetooth.

Figure 9:
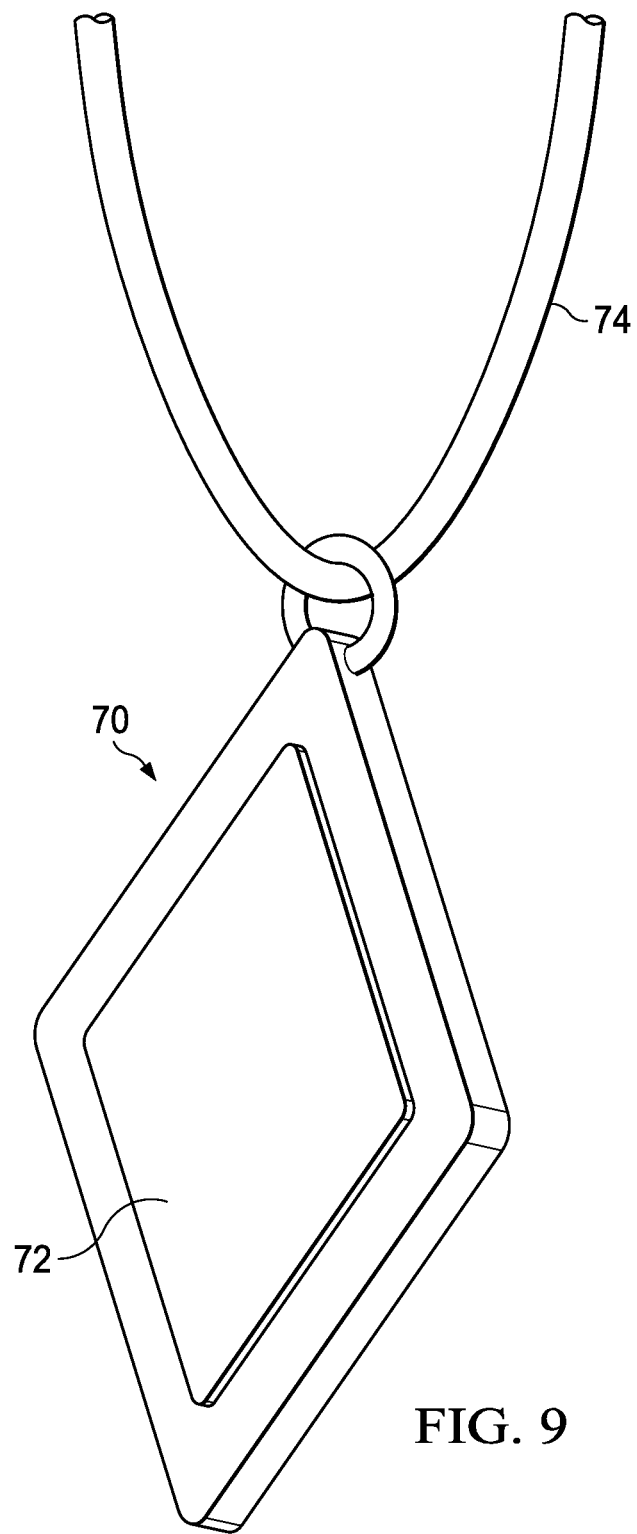
FIG. 9 is a top perspective view of a secondary transmitter.

FIG. 9 depicts another example of an exemplary peripheral device—a secondary transmitter 70. The secondary transmitter 70 may be connected to the device 100 by any suitable means (e.g., over WIFI or though Bluetooth), and may be used to initiate a call when the user presses the call button 72 on the secondary transmitter 70. Component and programming solutions for the secondary transmitter 70 will be apparent to those skilled in the art. The call recipient may be the same as, or different than, the predetermined call recipients associated with the call buttons 20 on the device 100. In one or more embodiments, additional call buttons may be provided on the secondary transmitter 70 and configured to initiate calls to additional call recipients. Further, it is contemplated that the secondary transmitter 70 may be provided with a wearable feature (e.g., lanyard 74, watch straps, belt clip, etc.) to help keep the secondary transmitter 70 on the user's person. In doing so, a quicker, easier-to-access way of operating the various features of the device 100 may be provided. The secondary transmitter 70 may also include various stand-alone features that are operable without being coupled to the device 100. These stand-alone features may include, for example, a radio, a flashlight, a wireless communication system, and the like.

Figure 10:
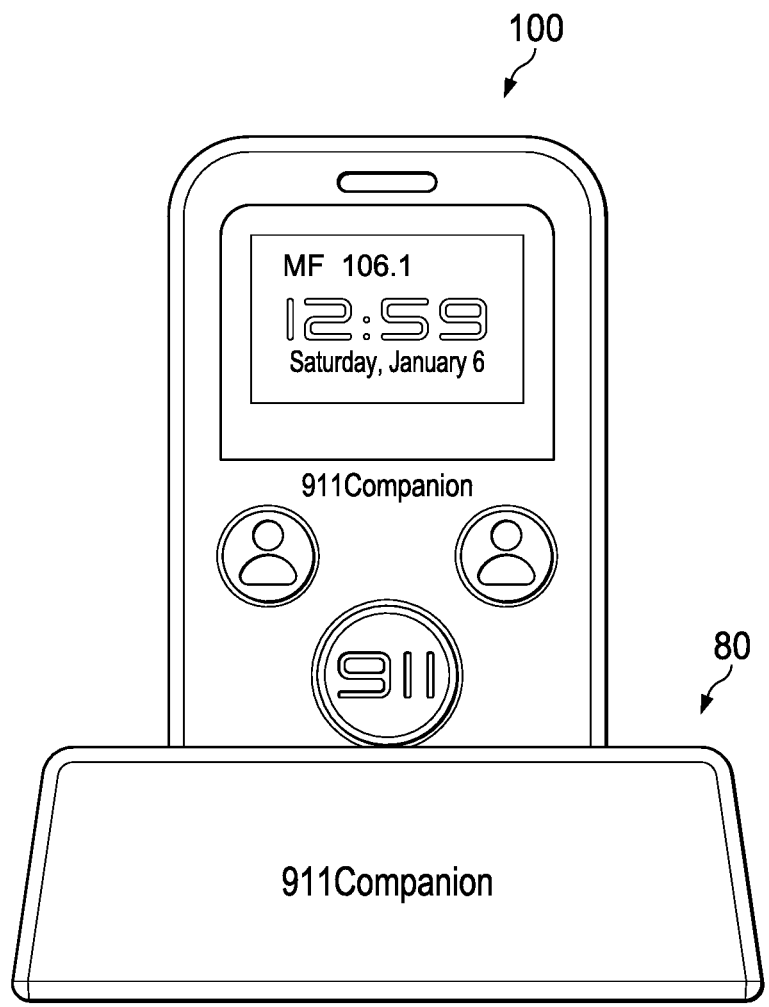
FIG. 10 is a front elevational view of the medical alert device of FIG. 1 being received by a charging cradle.
Figure 12:
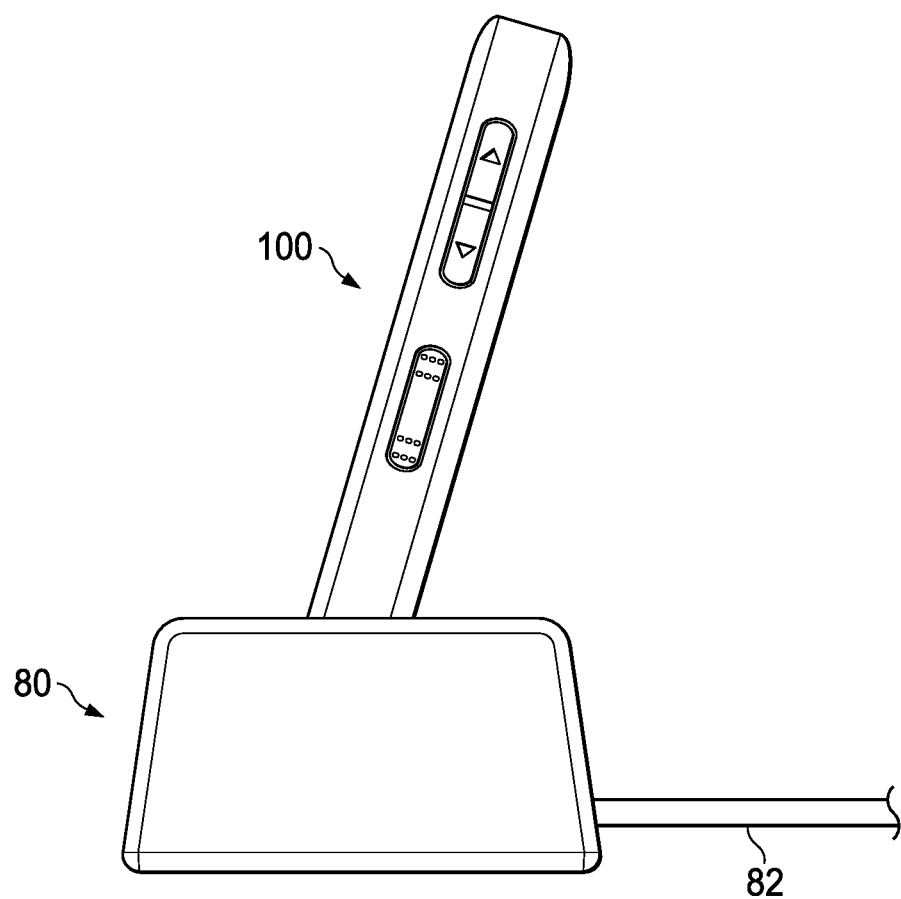
FIG. 12 is a right-side elevational view of the medical alert device and the charging cradle of FIG. 10.
Figure 11:
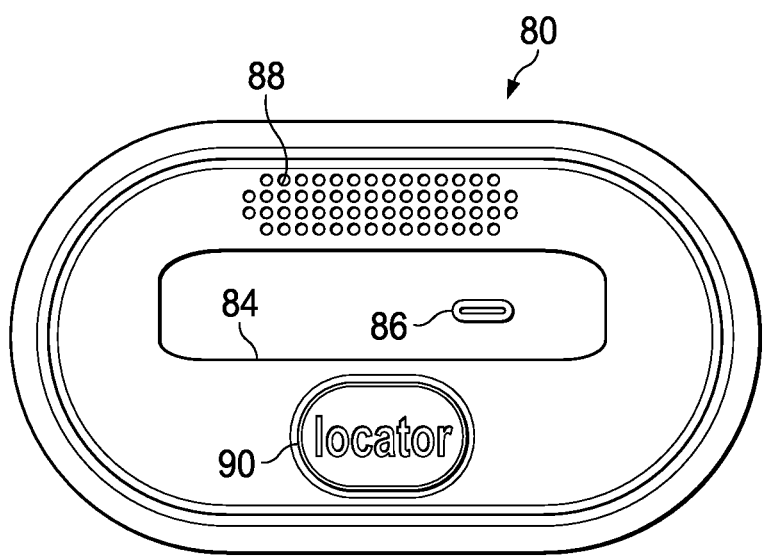
FIG. 11 is a top plan view of the charging cradle of FIG. 10 without the medical alert device.

FIGS. 10-12 depicts yet another example of an exemplary peripheral device—a charging cradle 80. The charging cradle 80 may be configured to receive, connect to, and charge the device 100. Power may be supplied to the charging cradle 80 through a standard wall outlet electrical cord 82, such as those that include a Type A or Type B power plug, or an internal battery. As shown, the charging cradle 80 may define a receiving cavity 84 (shown as being recessed into the top surface of the charging cradle 80) and a coupling feature 86 positioned within the receiving cavity 84. The receiving cavity 84 may be configured to receive the bottom of the device 100 and, upon being received, may orient the device 100 upright at a slight backwards tilt (e.g., like a picture frame). The coupling feature 86 may couple with the port 42 on the bottom side of the device 100. Additionally, or alternatively, the charging cradle 80 may also be configured to provide for pass-through functionality when the device 100 is received in the charging cradle 80. For example, the charging cradle 80 may include a speaker 88 and/or a microphone configured to broadcast voice messages from the device 100 and/or receive voice messages from the user. If included, it is generally contemplated that a charging cradle speaker 88 should enable the user to hear voice messages from a greater distance compared to the speaker 14 on the device 100. Further, as best shown in FIG. 10, a charging cradle microphone may be particularly desirable because the depth of the receiving cavity 84 may block the microphone 16 on the device 100.

The charging cradle 80 may further be provided with a locate button 90 to help the user locate the device 100. The locate button 90 is shown as being generally elliptical in shape, located on the top surface of the charging cradle 80, and centered along its width. By pressing (i.e., actuating) the locate button 90, the charging cradle 80 may transmit a signal to the device 100 by way of, for example, WIFI or Bluetooth. The charging cradle may be provided with a transceiver, or similar component, capable of transmitting this signal. Upon receiving the signal, the device 100 may be programmed to broadcast a sound or some other audio response in an effort to reveal the location of the device 100.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A medical alert device comprising:
a body that defines an interior space for electronic components;
a microprocessor housed within the body that is configured to control the operation of the device;
a data store housed within the body that is configured to store a phone number of at least one predetermined call recipient;
a wireless communication module housed within the body that is connectable to a wireless network;
a preprogrammed user actuatable button supported by the body that is configured to, upon being actuated, initiate the execution of software instructions by the microprocessor to retrieve a phone number stored on the data store, connect to the wireless network, and establish a communication link with an emergency dispatch office by dialing the phone number;
at most, two additional preprogrammed user actuatable buttons, wherein each of the additional preprogrammed user actuatable buttons each, upon being actuated, initiate the execution of software instructions by the microprocessor to retrieve a different phone number from the data store, not associated with the emergency dispatch office, and establish a communication link over a wireless network by dialing the different phone number, wherein the communication link is configured to enable a user to hear and speak with a predetermined call recipient of the different phone number than the emergency dispatch office;
a display screen configured to show a battery level, a wireless connection status, a time, a date, a text message;
a speaker configured to be used from 4 to 18 inches away;
a microphone configured to be used from 4 to 18 inches away;
an amplifier configured to increase volume and sound quality;
a flashlight;
an emergency radio configured to tune into advisory radio stations;
an on/off button;
an AM/FM radio;
a headphone jack; and
a fall detector configured to automatically initiate a call to one of the predetermined call recipient when a user experiences a fall.

2. The medical alert device of claim 1 wherein:
the data store is further configured to store prerecorded messages; and
the software instructions executable by the microprocessor is configured to retrieve a prerecorded message from the data store and transmit the prerecorded message to the call recipient upon the establishment of a communication link.

3. The medical alert device of claim 1 wherein:
the medical alert device further comprises a fall detector configured to detect the occurrence of a fall; and
the microprocessor is configured to automatically initiate, upon detecting a fall, the execution of software instructions to retrieve the phone number stored on the data store, connect to the wireless network, and establish a communication link with the predetermined call recipient by dialing the phone number.

4. The medical alert device of claim 1 further comprising:
a tracking system configured to track the geographic location of the user.

5. The medical alert device of claim 4 wherein:
the tracking system and the microprocessor is configured to transmit the user's location to a call recipient upon the establishment of a communication link.

6. The medical alert device of claim 1 wherein:
the microphone and the speaker configured to receive and broadcast, respectively, communications between a call recipient and user.

7. The medical alert device of claim 1 further comprising:
a radio configured to receive radio broadcast signals.

8. The medical alert device of claim 1 further comprising:
a standard telephone keypad configured to receive user input.

9. The medical alert device of claim 1 further comprising:
a wearable feature comprising at least one of a lanyard, watch straps, and a belt clip.

10. A medical alert device comprising:
a body that defines an interior space for electronic components;
a microprocessor housed within the body that is configured to control the operation of the device;
a data store housed within the body that is configured to store a first phone number of a first predetermined call recipient, a second phone number of a second predetermined call recipient, and a third phone number of a third predetermined call recipient;
a reader at least partially housed within the body that is configured to receive a subscriber identity module identification card (SIM card);
a limited use SIM card that is insertable into the reader and configured to identify and authenticate a user of the device, wherein the limited use SIM card is configured to allow emergency calls;
a wireless communication module housed within the body that is operable with the limited use SIM card and connectable to a cellular network;
a first preprogrammed user actuatable button supported by the body that is configured to, upon being actuated, initiate the execution of software instructions by the microprocessor to retrieve the first phone number stored on the data store, connect to the cellular network, and establish a communication link with the first predetermined call recipient by dialing the first phone number, wherein the first predetermined call recipient is the emergency dispatch office, wherein the emergency dispatch office is independent of a subscription based monitoring service;
a second and third preprogrammed user actuatable buttons supported by the body, wherein the second and third preprogrammed user actuatable buttons are configured to, upon being actuated, initiate the execution of software instructions by the microprocessor to retrieve the second phone number or the third phone number stored on the data store, connect to the cellular network, and establish a communication link with the second or third predetermined call recipient by dialing the second or third phone number, wherein the device is configured to receive calls only initiated from the predetermined call recipients and the emergency dispatch office;
a display screen configured to show a battery level, a wireless connection status, a time, a date, a text message;
a speaker configured to be used from 4 to 18 inches away;
a microphone configured to be used from 4 to 18 inches away;
an amplifier configured to increase volume and sound quality;
a flashlight;
an emergency radio configured to tune into advisory radio stations;
an on/off button;
an AM/FM radio;
a headphone jack; and
a fall detector configured to automatically initiate a call to one of the predetermined call recipient when a user experiences a fall.

11. The medical alert device of claim 10 wherein:
the SIM card is a limited use SIM card that is configured to only require a one-time fee before identifying and authenticating a user of the cellular device.

12. The medical alert device of claim 10 wherein:
the limited use SIM card is further configured to enable a limited number of calls on the cellular device.

13. A medical alert device comprising:
a body that defines an interior space for electronic components and includes a front face;
a microprocessor housed within the body that is configured to control the operation of the device;
a data store housed within the body that is configured to store a phone number of a predetermined call recipient;
a wireless communication module housed within the body that is connectable to a wireless network;
a plurality of buttons positioned on a front face of the body, wherein the plurality of buttons consists of:
a first preprogrammed user actuatable button, and a pair of second preprogrammed user actuatable buttons, wherein the first preprogrammed user actuatable button supported by the body that is configured to, upon being actuated, initiate the execution of software instructions by the microprocessor to retrieve a phone number stored on the data store, connect to the wireless network, and establish a communication link with an emergency call center by dialing the phone number, wherein the phone number is independent of a subscription based monitoring service, wherein the pair of second preprogrammed user actuatable buttons are configured to allow a user to choose between the pair of preprogrammed user actuatable buttons based upon considerations of the needs of a user, wherein upon being actuated each of the preprogrammed user actuatable buttons initiates the execution of software instructions by the microprocessor to retrieve one of the pair of phone numbers stored on the data store, connects to the wireless network, and establish a communication link with one of two separate predetermined call recipient by dialing one of the pair of phone numbers; and
a display screen configured to show a battery level, a wireless connection status, a time, a date, a text message;
a speaker configured to be used from 4 to 18 inches away;
a microphone configured to be used from 4 to 18 inches away;
an amplifier configured to increase volume and sound quality;
a flashlight;
an emergency radio configured to tune into advisory radio stations;
an on/off button;
an AM/FM radio;
a headphone jack; and
a fall detector configured to automatically initiate a call to one of the predetermined call recipient when a user experiences a fall.

14. The medical alert device of claim 13, further comprising:
a tracking system configured to transmit the user's location by way of a global positioning system to the predetermined call recipient when a user experiences a fall.

15. A medical alert system comprising:
the medical alert device of claim 1, and
a secondary transmitter separate and apart from the medical alert device, wherein the secondary transmitter is configured to be secured to a user's person and connected to the medical alert device by a WIFI or a Bluetooth, wherein the secondary transmitter includes a diamond shaped housing with a diamond shaped preprogrammed user actuatable button centered within the diamond shaped housing, wherein the diamond shaped preprogrammed user actuatable button is configured to, upon being actuated, initiate the execution of software instructions by the microprocessor to retrieve a phone number stored on the data store, connect to the wireless network, and establish a communication link with the emergency dispatch office by dialing the phone number.

16. The medical alert device of claim 13, further comprising:
a selectively detachable QUERTY keypad; and
a tracking system configured to transmits the user's location by way of a global positioning system to the predetermined call recipient.

17. The medical alert device of claim 16, further comprising:
An inscription including medical information positioned on a back face of the body;
a battery;
a wireless communication module; and
a SIM card.

\* \* \* \* \*